US011285194B2

(12) United States Patent
Szalay et al.

(10) Patent No.: US 11,285,194 B2
(45) Date of Patent: Mar. 29, 2022

(54) COMBINATION IMMUNOTHERAPY APPROACH FOR TREATMENT OF CANCER

(71) Applicant: CALIDI BIOTHERAPEUTICS, INC., La Jolla, CA (US)

(72) Inventors: Aladar Szalay, Highland, CA (US); Boris Minev, San Diego, CA (US)

(73) Assignee: Calidi Biotherapeutics, Inc., La Jolla, CA (US)

( * ) Notice: Subject to any disclaimer, the term of this patent is extended or adjusted under 35 U.S.C. 154(b) by 0 days.

(21) Appl. No.: 15/521,602

(22) PCT Filed: Oct. 23, 2015

(86) PCT No.: PCT/US2015/057234
§ 371 (c)(1),
(2) Date: Apr. 24, 2017

(87) PCT Pub. No.: WO2016/065330
PCT Pub. Date: Apr. 28, 2016

(65) Prior Publication Data
US 2017/0239338 A1 Aug. 24, 2017

Related U.S. Application Data

(60) Provisional application No. 62/073,907, filed on Oct. 31, 2014, provisional application No. 62/068,557, filed on Oct. 24, 2014.

(51) Int. Cl.
| | | |
|---|---|---|
| A61K 39/00 | (2006.01) |
| A61K 45/06 | (2006.01) |
| A61K 35/54 | (2015.01) |
| A61K 31/00 | (2006.01) |
| A61K 35/44 | (2015.01) |
| A61K 38/50 | (2006.01) |
| A61K 35/28 | (2015.01) |
| A61K 35/51 | (2015.01) |
| A61K 41/00 | (2020.01) |
| A61K 35/30 | (2015.01) |
| A61K 35/768 | (2015.01) |
| A61K 9/00 | (2006.01) |
| A61K 35/12 | (2015.01) |
| A61K 38/19 | (2006.01) |
| A61K 39/395 | (2006.01) |
| A61N 5/06 | (2006.01) |
| A61N 5/10 | (2006.01) |
| C07K 16/28 | (2006.01) |
| C07K 16/30 | (2006.01) |

(52) U.S. Cl.
CPC ........ *A61K 39/0011* (2013.01); *A61K 9/0019* (2013.01); *A61K 31/00* (2013.01); *A61K 35/12* (2013.01); *A61K 35/28* (2013.01); *A61K 35/30* (2013.01); *A61K 35/44* (2013.01); *A61K 35/51* (2013.01); *A61K 35/54* (2013.01); *A61K 35/768* (2013.01); *A61K 38/19* (2013.01); *A61K 38/50* (2013.01); *A61K 39/39558* (2013.01); *A61K 41/0038* (2013.01); *A61K 45/06* (2013.01); *A61N 5/062* (2013.01); *A61N 5/10* (2013.01); *C07K 16/2818* (2013.01); *C07K 16/30* (2013.01); *C12Y 305/01001* (2013.01); *A61K 2039/5156* (2013.01); *A61K 2039/572* (2013.01); *A61N 2005/0661* (2013.01); *A61N 2005/1098* (2013.01); *C07K 2317/76* (2013.01)

(58) Field of Classification Search
CPC .... A61K 39/0011; A61K 35/54; A61K 31/00; A61K 35/44; A61K 38/50; A61K 35/28; A61K 35/51; A61K 41/0038; A61K 35/30; A61K 35/768; A61K 9/0019; A61K 35/12; A61K 38/19; A61K 39/39558; A61K 45/06; A61K 2039/572; C12Y 305/01001; A61N 5/062; A61N 5/10; A61N 2005/0661; A61N 2005/1098; C07K 16/2818; C07K 16/30; C07K 2317/76
See application file for complete search history.

(56) References Cited

U.S. PATENT DOCUMENTS

| | | | |
|---|---|---|---|
| 7,588,771 B2 | 9/2009 | Szalay et al. | 424/232.1 |
| 7,662,398 B2 | 2/2010 | Szalay et al. | 424/232.1 |
| 7,754,221 B2 | 7/2010 | Szalay et al. | 424/199.1 |

(Continued)

FOREIGN PATENT DOCUMENTS

| | | |
|---|---|---|
| WO | WO 2008/009115 | 1/2008 |
| WO | WO 2008/052054 | 5/2008 |

(Continued)

OTHER PUBLICATIONS

Studeny et al. "Mesenchymal stem cells: potential precursors for tumor stroma and targeted-delivery vehicles for anticancer agents." J Natl Cancer Inst. Nov. 3, 2004;96(21):1593-603. (Year: 2004).*

(Continued)

*Primary Examiner* — Titilayo Moloye
(74) *Attorney, Agent, or Firm* — Dentons US LLP; Stephanie Seidman (57) ABSTRACT

Disclosed herein are methods and compositions related to combination therapy for cancer. More specifically, several treatment modalities are used in combination to induce an effective anti-tumor immune response. The present invention relates generally to the treatment of human cancer and, more specifically, to use of several treatment modalities in combination to induce effective anti-tumor immune responses.

16 Claims, 2 Drawing Sheets

(56) References Cited

U.S. PATENT DOCUMENTS

| | | | | |
|---|---|---|---|---|
| 8,021,662 | B2 | 9/2011 | Szalay et al. | 424/138.1 |
| 8,221,769 | B2 | 7/2012 | Szalay et al. | 424/232.1 |
| 8,859,256 | B2 | 10/2014 | Szalay et al. | 435/210 |
| 9,492,534 | B2 | 11/2016 | Szalay et al. | 424/199.1 |
| 10,105,436 | B2 | 10/2018 | Szalay et al. | 424/186.1 |
| 2002/0168344 | A1 | 11/2002 | Coffey et al. | 424/93.2 |
| 2004/0072775 | A1 | 4/2004 | Sobol et al. | |
| 2007/0086984 | A1 | 4/2007 | Coffey et al. | 424/93.2 |
| 2007/0264231 | A1 | 11/2007 | Gianni et al. | 424/93.1 |
| 2008/0206201 | A1 | 8/2008 | Beier et al. | 424/93.6 |
| 2009/0117082 | A1 | 5/2009 | Lee et al. | 424/93.6 |
| 2009/0162288 | A1* | 6/2009 | Chen | A61K 31/70 424/9.3 |
| 2009/0324616 | A1* | 12/2009 | Stassi | G01N 33/57484 424/174.1 |
| 2010/0055102 | A1* | 3/2010 | Langermann | A61K 31/675 424/134.1 |
| 2010/0297072 | A1 | 11/2010 | Depinho | 424/85.2 |
| 2011/0027239 | A1* | 2/2011 | Paek | C12N 15/111 424/93.21 |
| 2011/0064650 | A1 | 3/2011 | Szalay | 424/1.11 |
| 2011/0171219 | A1 | 7/2011 | Merchant | |
| 2012/0087901 | A1* | 4/2012 | Nelson | C12N 5/0663 424/93.21 |
| 2013/0273007 | A1 | 10/2013 | Szalay et al. | 424/93.2 |
| 2014/0017787 | A1* | 1/2014 | Betancourt | A61K 35/28 435/375 |
| 2014/0271677 | A1* | 9/2014 | Palese | A61P 35/00 424/172.1 |
| 2015/0086541 | A1* | 3/2015 | Aguilar-Cordova | A61K 31/522 424/133.1 |
| 2015/0352206 | A1* | 12/2015 | Gajewski | A61K 31/4245 424/142.1 |
| 2017/0043010 | A1 | 2/2017 | Szalay et al. | 424/186.1 |
| 2018/0092951 | A1 | 4/2018 | Szalay et al. | 424/138.1 |
| 2018/0326048 | A1 | 11/2018 | Szalay et al. | 424/186.1 |
| 2019/0367880 | A1 | 12/2019 | Draganov et al. | 424/93.21 |
| 2020/0140824 | A1 | 5/2020 | Fernandez Santidrian et al. | 424/93.21 |

FOREIGN PATENT DOCUMENTS

| | | | |
|---|---|---|---|
| WO | WO 2009/139921 | 11/2009 | |
| WO | WO-2011070974 A1 * | 6/2011 | C12N 5/0667 |
| WO | WO2012/061120 A1 | 5/2012 | |
| WO | WO-2013112942 A1 * | 8/2013 | G01N 33/57484 |
| WO | WO 2014/022138 | 2/2014 | |
| WO | WO 2014/066834 | 5/2014 | |
| WO | WO 2015/089280 | 6/2015 | |
| WO | WO 2016/008976 | 1/2016 | |
| WO | WO 2016/065330 | 4/2016 | |
| WO | WO 2016/149559 | 9/2016 | |
| WO | WO 2017/027757 | 2/2017 | |
| WO | WO 2019/236633 | 12/2019 | |
| WO | WO 2020/097269 | 5/2020 | |
| WO | WO 2020/247385 | 12/2020 | |

OTHER PUBLICATIONS

Waterman et al. "A New Mesenchymal Stem Cell (MSC) Paradigm: Polarization into a Pro-Inflammatory MSC1 or an Immunosuppressive MSC2 Phenotype." PLoS One. 2010; 5(4): e10088. (Year: 2012).*

Yuan et al. "Interleukin-23-expressing bone marrow-derived neural stem-like cells exhibit antitumor activity against intracranial glioma." Cancer Res. Mar. 1, 2006;66(5):2630-8. (Year: 2006).*

Yang et al. "Adult neural stem cells expressing IL-10 confer potent immunomodulation and remyelination in experimental autoimmune encephalitis." J Clin Invest. Dec. 2009;119(12):3678-91. (Year: 2009).*

Kang et al. "Neurogenesis of Rhesus adipose stromal cells." J Cell Sci. Aug. 15, 2004;117(Pt 18):4289-99. Epub Aug. 3, 2004. (Year: 2004).*

Josiah et al. "Adipose-derived stem cells as therapeutic delivery vehicles of an oncolytic virus for glioblastoma." Mol Ther. Feb. 2010; 18(2):377-85 (Year: 2010).*

Deng et al. "Irradiation and anti-PD-L1 treatment synergistically promote antitumor immunity in mice." J Clin Invest. Feb. 2014;124(2):687-95. doi: 10.1172/JCI67313. Epub Jan. 2, 2014. (Year: 2014).*

Castella et al. "Adipose-derived stromal cells: Their identity and uses in clinical trials, an update." World J Stem Cells. Apr. 26, 2011;3(4):25-33. (Year: 2011).*

Wang et al. "The Synergistic In Vitro and In Vivo Antitumor Effect of Combination Therapy with Salinomycin and 5-Fluorouracil against Hepatocellular Carcinoma." PLoS One. May 9, 2014;9(5):e97414. (Year: 2014).*

Lesterhuis et al. "Synergistic Effect of CTLA-4 Blockade and Cancer Chemotherapy in the Induction of Anti-Tumor Immunity." PLoS One. Apr. 23, 2013;8(4):e61895 (Year: 2013).*

Dias et al. "Targeted cancer immunotherapy with oncolytic adenovirus coding for a fully human monoclonal antibody specific for CTLA-4." Gene Therapy vol. 19, pp. 988-998(2012) (Year: 2011).*

Gao et al. "Recombinant vesicular stomatitis virus targeted to Her2/neu combined with anti-CTLA4 antibody eliminates implanted mammary tumors." Cancer Gene Therapy vol. 16, pp. 44-52(2009) (Year: 2009).*

Hwa et al. "Role of Toll-Like Receptors on Human Adipose-Derived Stromal Cells." Stem Cells. Dec. 2006;24(12):2744-52. (Year: 2006).*

Hamid et al. "Clinical activity, safety, and biomarkers of MPDL3280A, an engineered PD-L1 antibody in patients with locally advanced or metastatic melanoma (mM)." Journal of Clinical Oncology 31, No. 15_suppl (May 20, 2013) 9010-9010. (Year: 2013).*

Lamfers et al. "Homing properties of adipose-derived stem cells to intracerebral glioma and the effects of adenovirus infection." Cancer Lett. Feb. 8, 2009;274(1):78-87. (Year: 2009).*

Lombardo et al. "Toll-like receptor-mediated signaling in human adipose-derived stem cells: implications for immunogenicity and immunosuppressive potential." Tissue Eng Part A Jul. 2009; 15(7):1579-89. (Year: 2009).*

Advani et al. "Viral Oncolysis." Holland-Frei Cancer Medicine. 6th edition. Hamilton (ON): BC Decker; 2003. Available from: https://www.ncbi.nlm.nih.gov/books/NBK13520/ (Year: 2003).*

Draghiclu, O. et al., Therapeutic immunization and local low-dose tumor irradiation, a reinforcing combination, International Journal of Cancer, 2013, 134, pp. 859-872.

International Search Report and Written Opinion dated Dec. 9, 2015, for International Application No. PCT/US2015/057234.

Letter/Written Disclosure of the Supplemental Information Disclosure Statement for the above-referenced application, filed herewith on May 24, 2018, 2 pages.

Ahmed et al., "The Lister Strain of Vaccinia Virus as an Anticancer Therapeutic Agent," Chapter 16 in Gene Therapy of Cancer (Third Edition) p. 225-238 (2014).

Brader et al., "Imaging a Genetically Engineered Oncolytic Vaccinia Virus (GLV-1h99) using a human norepinephrine transporter (hNET) reporter gene," Clin. Cancer Res. 15(11):3791-3801 (2009).

Brader et al., "Imaging of Lymph Node Micrometastases Using an Oncolytic Herpes Virus and [18F]FEAU PET," PLoS ONE 4(3):e4789 (2009).

Buckel et al., "Combination of fractionated irradiation with anti-VEGF expressing vaccinia virus therapy enhances tumor control by simultaneous radiosensitization of tumor associated endothelium," Int J Cancer 133: 2989-2999 (2013).

Cancer Facts and Figures American Cancer Society: Atlanta, GA (2008) (72 pages).

Chen et al., "A Novel Recombinant Vaccinia Virus Expressing the Human Norepinephrine Transporter Retains Oncolytic Potential and Facilitates Deep-Tissue Imaging", Mol. Med. 15(5-6): 144-151 (2009) (Epub ahead of print).

Choi et al., "Correlation of Computed Tomography and Positron Emission Tomography in Patients with Metastatic Gastrointestinal (56) References Cited

OTHER PUBLICATIONS

Stromal Tumor Treated at a Single Institution with Imatinib Mesylate: Proposal of New Computed Tomography Response Criteria," J Clin Oncology 25(13): 1753-1759 (2007).
Frentzen et al., "Anti-VEGF single-chain antibody GLAF-1 encoded by oncolytic vaccinia virus significantly enhances antitumor therapy," Proc Natl Acad Sci 106(31): 12915-12920 (2009).
Hang-Fu et al., "Liposuction Fat-Fillant Implant for Breast Augmentation and Reconstruction," Aesthetic Plastic Surgery 19(5): 427-437 (1995).
Huang, T., "Vaccinia Virus-mediated Therapy of Solid Tumor Xenografts: Intra-tumoral Delivery of Therapeutic Antibodies," Dissertation (2013), 172 pages.
Iovino et al., "Immunotherapy targeting colon cancer stem cells," Immunotherapy 3(1): 97-106 (2011).
Josiah et al., "Adipose-derived Stem Cells as Therapeutic Delivery Vehicles of an Oncolytic Virus for Glioblastoma," Mol Ther 18(2): 277-285 (2010).
Kim et al., "Stem Cell-Based Cell Carrier for Targeted Oncolytic Virotherapy: Translational Opportunity and Open Questions," Viruses 7: 6200-6217 (2015).
Kurita et al., "Influences of centrifugation on cells and tissues in liposuction aspirates: optimized centrifugation for lipotransfer and cell isolation," Plastic and Reconstructive Surgery 121(3): 1033-1041 (2008), 11 pages.
Li et al., "Adjuvant effect of anti-4-1BB mAb administration in adoptive T cell therapy of cancer," Int J Biol Sci 3(7):455-462 (2007).
Mader et al., "Mesenchymal stem cell carriers protect oncolytic measles viruses from antibody neutralization in an orthotopic ovarian cancer therapy model," Clin Cancer Res 15(23): 7246-7255 (2009), 18 pages.
Mader et al., "Optimizing patient derived mesenchymal stem cells as virus carriers for a Phase I clinical trial in ovarian cancer," J Trans Med 11: 20 (2013), 14 pages.
Munguia et al., "Cell carriers to deliver oncolytic viruses to sites of myeloma tumor growth," Gene Ther 15(10): 797-806 (2008).
Patil et al., "Virotherapy of Canine Tumors with Oncolytic Vaccinia Virus GLV-1h109 Expressing an Anti-VEGF Single-Chain Antibody," PLoS One 7(10): e47472 (2012).
Power, A.T. and J.C. Bell, "Cell-based Delivery of Oncolytic Viruses: A New Strategic Alliance for a Biological Strike Against Cancer," Mol Ther 15(4): 660-665 (2007).
Protest Documents Submitted Under 37 CFR § 1.99 on Aug. 7, 2009 in connection with U.S. Appl. No. 12/218,953, 53 pages.
Response, filed Aug. 17, 2009, to Third Party Submission of Protest Documents Submitted Under 37 CFR § 1.99 on Aug. 7, 2009, in connection with U.S. Appl. No. 12/218,953, 5 pages.
Roy, D. G. and J. C. Bell, "Cell carriers for oncolytic viruses: current challenges and future directions," Oncolytic Virother 2: 47-56 (2013).
Quetglas et al., "Immunotherapeutic Synergy Between Anti-CD137 mAb and Intratumoral Administration of a Cytopathic Semliki Forest Virus Encoding IL-12," Mol Ther 20(9):1664-1675 (2012).
Thorne et al., "Vaccinia virus and oncolytic virotherapy of cancer," Curr Opin Mol Ther 7(4): 359-365 (2005).
Wolchok et al., "Guidelines for the Evaluation of Immune Therapy Activity in Solid Tumors: Immune-Related Response Criteria," Clinical Cancer Research 15(23): 7412-7420 (2009).
Yokouchi et al., "Anti-OX40 monoclonal antibody therapy in combination with radiotherapy results in therapeutic antitumor immunity to murine lung cancer," Cancer Sci 99(2):361-367 (2008).
Yoshimura et al., "Cell-Assisted Lipotransfer for Cosmetic Breast Augmentation: Supportive Use of Adipose-Derived Stem/Stromal Cells," Aesthetic Plastic Surgery 32(1): 48-55 (2008).
Zamarin et al., "Localized Oncolytic Virotherapy Overcomes Systemic Tumor Resistance to Immune Checkpoint Blockade Immunotherapy," Sci Trans Med 6(226): 226ra32, 14 pages.

Zeh et al., "First-in-man Study of Western Reserve Strain Oncolytic Vaccinia Virus: Safety, Systemic Spread, and Antitumor Activity," Mol Ther23(1): 202-214 (2015).
Zhang et al., "Eradication of Solid Human Breast Tumors in Nude Mice with an Intravenously Injected Light-Emitting Oncolytic Vaccinia Virus," Cancer Research 67(20): 10038-10046 (2007).
International Preliminary Report on Patentability, dated Apr. 25, 2017, in connection with corresponding International Patent Application No. PCT/US2015/057234, 5 pages.
Supplementary European Search Report, dated May 23, 2018, issued in connection with corresponding European Patent Application No. 15852615.2, 7 pages.
Search Report and Written Opinion, dated Apr. 6, 2018, in connection with corresponding Singaporean Patent Application No. 11201703326S, 11 pages.
International Preliminary Report on Patentability, dated Sep. 28, 2017, in connection with International Patent Publication No. PCT/US2016/022978, 10 pages.
International Search Report and Written Opinion, dated Jul. 27, 2016, in connection with International Patent Publication No. PCT/US2016/022978, 12 pages.
Office Action, dated Dec. 1, 2017, in connection with U.S. Appl. No. 15/235,082, 8 pages.
Response, filed Mar. 1, 2018, to Office Action, dated Dec. 1, 2017, in connection with U.S. Appl. No. 15/235,082, 8 pages.
Notice of Allowance, dated May 1, 2018, in connection with U.S. Appl. No. 15/235,082, 8 pages.
International Search Report and Written Opinion, dated Feb. 6, 2017, in connection with International Patent Application No. PCT/US2016/046647, 14 pages.
International Preliminary Report on Patentability, dated Feb. 13, 2018, in connection with International Patent Application No. PCT/US2016/046647, 10 pages.
U.S. Appl. No. 15/235,082, filed Aug. 11, 2016, 2017/0043010, Feb. 16, 2017.
Letter/Written Disclosure of the Supplemental Information Disclosure Statement for the above-referenced application, filed herewith on Nov. 29, 2018, 2 pages.
Mell et al., "Phase I Trial of Intravenous Oncolytic Vaccinia Virus (GL-ONC1) with Cisplatin and Radiotherapy in Patients with Locoregionally Advanced Head and Neck Carcinoma," Clin. Cancer Res. 23(19):5696-5702 (2017).
Minev et al., "First in man study of TK positive oncolytic vaccinia virus delivered by adipose stromal vascular fraction cells," [abstract] Journal for ImmunoTherapy of Cancer 2018, 6(Suppl 1):115, Abstract No. P609, Nov. 2018, 2 pages.
Santidrian et al., "A cell-based platform to protect and enhance oncolytic virus therapies," [abstract] Journal for ImmunoTherapy of Cancer 2018, 6(Suppl 1):115, Abstract No. P617, Nov. 2018, 1 page.
News Release, Calidi Biotherapeutics "Calidi Biotherapeutics Announces Two Abstracts Accepted for Presentation at the Society for Immunotherapy of Cancer's (SITC) 33rd Annual Meeting." Published Nov. 6, 2018 [online] Retrieved from: <URL: calidibio.com/2018/11/06/calidi-biotherapeutics-inc-granted-new-patent-from-uspto-for-cell-based-delivery-of-oncolytic-vaccinia-viruses-2/ [retrieved on Nov. 29, 2018], 3 pages.
Response, filed Oct. 22, 2018, to Communication pursuant to Rules 70(2) and 70a(2) EPC, dated Jun. 8, 2018, in connection with corresponding European Patent Application No. 15852615.2, 6 pages.
Response, filed Aug. 29, 2018, to Search Report and Written Opinion, dated Apr. 6, 2018, in connection with Singaporean Patent Application No. 11201703326S, 23 pages.
Updated Notice of Allowance, dated Aug. 21, 2018, in connection with U.S. Appl. No. 15/235,082, 6 pages.
Letter/Written Disclosure of the Supplemental Information Disclosure Statement for the above-referenced application, filed herewith on Jul. 18, 2019, 2 pages.
Berglund et al., "Immunoprivileged no more: measuring the immunogenicity of allogeneic adult mesenchymal stem cells," Stem Cell Research & Therapy 8:288 (2017), 7 pages.

(56) References Cited

OTHER PUBLICATIONS

Bolontrade et al., "A specific subpopulation of mesenchymal stromal cell carriers overrides melanoma resistance to an oncolytic adenovirus," Stem cells and development 21: 2689-2702 (2012), 28 pages.
De Souza Trindade et al., "Real-time PCR assay to identify variants of Vaccinia virus: implications for the diagnosis of bovine vaccinia in Brazil," J. Virol. Methods 152(1-2):63-71 (2008).
Huang et al., "The use of hypoxic cultured mesenchymal stem cell for oncolytic virus therapy," Cancer Gene Therapy 20: 308-316 (2013).
John et al., "Oncolytic Virus and Anti-4-1BB Combination Therapy Elicits Strong Antitumor Immunity against Established Cancer," Cancer Research 72(7): 1651-1660 (2012).
Kerrigan et al., "Mesenchymal stem cells for the delivery of oncolytic viruses in gliomas," Cytotherapy 19(4):445-457 (2017), 21 pages.
Lauer et al., "Phase I Study of Oncolytic Vaccinia Virus GL-ONC1 in Patients with Peritoneal Carcinomatosis," Clin. Cancer Res. 24(18):4388-4398 (2018).
Martinez-Quintanilla et al., "Encapsulated stem cells loaded with hyaluronidase-expressing oncolytic virus for brain tumor therapy," Mol Ther 23(1): 108-118 (2015).
Msaouel et al., "Oncolytic measles virus strains as novel anticancer agents," Expert Opin. Biol. Ther. 13(4):483-502 (2013), 28 pages.
Nakashima et al., "Directing systemic oncolytic viral delivery to tumors via carrier cells." Cytokine & Growth Factor Reviews 21(2-3): 119-126 (2010), 17 pages.
Ramirez et al., "Patient-derived mesenchymal stem cells as delivery vehicles for oncolytic virotherapy: novel state-of-the-art technology," Oncolytic Virotherapy 4:149-155 (2015).
Thorne et al., "Targeting localized immune suppression within the tumor through repeat cycles of immune cell-oncolytic virus combination therapy," Molecular Therapy 18(9): 1698-1705 (2010).
News Release, "Calidi Biotherapeutics Announces A Collaborative Study With The National Institutes Of Health (NIH) On The Therapeutic Potential Of Oncolytic Viruses Delivered By Mesenchymal Stem Cells," Published May 28, 2019 [online] Retrieved from: <URL: prnewswire.com/news-releases/calidi-biotherapeutics-announces-a-collaborative-study-with-the-national-institutes-of-health-nih-on-the-therapeutic-potential-of-oncolytic-viruses-delivered-by-mesenchymal-stem-cells-300857135.html [retrieved on May 28, 2019], 3 pages.
Examiner's Report, dated Apr. 5, 2019, in connection with Australian Patent Application No 2015335607, 3 pages.
Examiner's Report, dated Nov. 22, 2018, in connection with Canadian Patent Application No. 3,003,133, 6 pages.
Response, filed Feb. 22, 2019, to Examiner's Report, dated Nov. 22, 2018, in connection with Canadian Patent Application No. 3,003,133, 60 pages.
Examiner's Report, dated Mar. 26, 2019, in connection with Canadian Patent Application No. 3,003,133, 5 pages.
Response, filed Jun. 21, 2019, Examiner's Report, dated Mar. 26, 2019, in connection with Canadian Patent Application No. 3,003,133, 36 pages.
Communication Pursuant to Article 94(3) EPC, dated Feb. 7, 2019, in connection with European Patent Application No. 15852615.2, 4 pages.
Response, filed Apr. 10, 2019, to Communication Pursuant to Article 94(3) EPC, dated Feb. 7, 2019, in connection with European Patent Application No. 15852615.2, 51 pages.
Office Action, dated Jul. 1, 2019, in connection with Israel Application No. 251890 [Original document in Hebrew and English translation], 4 pages.
Examination Report, dated Apr. 18, 2019, in connection with New Zealand Patent Application No. 732211, 5 pages.
English letter, dated Jun. 20, 2019, reporting Official Action, dated May 24, 2019, in connection with Russian Application No. 2017117889 [English letter and original document in Russian], 11 pages.
Written Opinion, dated May 9, 2019, in connection with Singaporean Patent Application No. 11201703326S, 9 pages.

Search Report and Written Opinion, dated Apr. 23, 2019, in connection with Singapore Patent Application No. 11201801177T, 11 pages.
Letter/Written Disclosure of the Supplemental Information Disclosure Statement for the above-referenced application, filed herewith on Oct. 10, 2019, 3 pages.
Examiner's Report, dated Sep. 6, 2019, in connection with Canadian Patent Application No. 3,003,133, 6 pages.
Letter/Written Disclosure of the Supplemental Information Disclosure Statement for the abovereferenced application, filed herewith on Aug. 16, 2019, 2 pages.
Communication Pursuant to Article 94(3) EPC, dated Jun. 27, 2019, in connection with European Patent Application No. 15852615.2, 5 pages.
Letter/Written Disclosure of the Supplemental Information Disclosure Statement for the above-referenced application, filed herewith on Jan. 17, 2020, 4 pages.
Examiner's report, dated Oct. 25, 2019, in connection with Australian Patent Application No. 2015335607, 3 pages.
Examination Report, dated Oct. 31, 2019, in connection with New Zealand Patent Application No. 732211, 5 pages.
Communication Pursuant to Article 94(3) EPC [claims deemed allowable], dated Jan. 7, 2020, in connection with European Patent Application No. 15852615.2, 4 pages.
Notification Prior to Acceptance, dated Oct. 27, 2019, in connection with Israel Application No. 251890 [Original document in Hebrew, English translation, and accepted claims in English], 11 pages.
English letter, dated Dec. 11, 2019, reporting Decision to Grant, dated Oct. 18, 2019, in connection with Russian Application No. 2017117889 [English letter and original document in Russian], 14 pages.
Guse et al., "Oncolytic vaccinia virus for the treatment of cancer," Expert Opin Biol Ther 11(5):595-608 (2011).
Letter/Written Disclosure of the Supplemental Information Disclosure Statement for the abover-eferenced application, filed herewith Feb. 10, 2020, 2 pages.
Ahmed et al., "A Comparative Study of Neural and Mesenchymal Stem Cell-Based Carriers for Oncolytic Adenovirus in a Model of Malignant Glioma," Mol Pharm 8(5): 1559-72 (2011).
Bourin et al., "Stromal cells from the adipose tissue-derived stromal vascular fraction and culture expanded adipose tissue-derived stromal/stem cells: a joint statement of the International Federation for Adipose Therapeutics and Science (IFATS) and the International Society for Cellular Therapy (ISCT)," Cytotherapy 15(6):641-648 (2013).
Cecil et al., "Vaccinia virus injected human tumors: oncolytic virus efficiency predicted by antigen profiling analysis fitted boolean models," Bioengineered 10(1):190-96 (2019).
W. M. Chan and G. McFadden, "Oncolytic Poxviruses," Annu Rev Virol 1(1): 119-141 (2014).
Draganov et al., "Delivery of oncolytic vaccinia virus by matched allogeneic stem cells overcomes critical innate and adaptive immune barriers," Transl Med. 17 (1): 100 (2019), 22 pages.
Kilinc et al., "The ratio of ADSCs to HSC-progenitors in adipose tissue derived SVF may provide the key to predict the outcome of stem-cell therapy," Clin Transl Med 7:5 (2018), 20 pages.
Lu et al., "Genetic engineering of dendritic cells to express immunosuppressive molecules (viral IL-10, TGF-beta, and CTLA4Ig)," J Leukoc Biol 66(2): 293-96 (1999).
Minev et al., "First-in-human study of TK-positive oncolytic vaccinia virus delivered by adipose stromal vascular fraction cells," Transl Med 17 (1): 271 (2019), 15 pages.
Moreno et al., "Human Menstrual Blood-Derived Mesenchymal Stem Cells as Potential Cell Carriers for Oncolytic Adenovirus," Stem Cells International 2017: 3615729 (2017), 10 pages.
Nguyen et al., "Vaccinia virus-mediated expression of human erythropoietin in tumors enhances virotherapy and alleviates cancer-related anemia in mice," Mol Ther 21(11): 2054-62 (2013).
Nishio et al., "Armed oncolytic virus enhances immune functions of chimeric antigen receptor-modified T cells in solid tumors," Cancer Res. 74(18):5195-5205 (2014).

(56) References Cited

OTHER PUBLICATIONS

Tsoneva et al., "Humanized Mice with Subcutaneous Human Solid Tumors for Immune Response Analysis of Vaccinia Virus-Mediated Oncolysis," Mol Ther Oncolytics 5:41-61 (2017).

Wang et al., "Oncolytic vaccinia virus GLV-1h68 strain shows enhanced replication in human breast cancer stem-like cells in comparison to breast cancer cells," J Transl Med 10:167 (2012), 15 pages.

Minev et al., "First in man study of TK positive oncolytic vaccinia virus delivered by adipose stromal vascular fraction cells," poster presented at The Society for Immunotherapy of Cancer's (SITC) 33rd Annual Meeting | Nov. 7-11, 2018 Washington, D.C., 1 page.

Santidrian et al., "A cell-based platform to potentiate oncolytic virus therapies," poster presented at The Society for Immunotherapy of Cancer's (SITC) 33rd Annual Meeting | Nov. 7-11, 2018 Washington, D.C., 1 page.

Invitation to Pay Additional Fees and Protest Fees, and International Search Report and Provisional Written Opinion, dated Dec. 13, 2019, in connection with International Patent Application No. PCT/US2019/035464, 28 pages.

Response, filed Jan. 10, 2020, to Invitation to Pay Additional Fees and Protest Fees, and International Search Report and Provisional Written Opinion, dated Dec. 13, 2019, in connection with International Patent Application No. PCT/US2019/035464, 14 pages.

Response, filed Oct. 23, 2019, to Examiner's report, dated Apr. 5, 2019, in connection with Australian Patent Application No. 2015335607, 19 pages.

Response, filed Dec. 6, 2019, to Examiner's Report, dated Sep. 6, 2019, in connection with Canadian Patent Application No. 3,003,133, 83 pages.

Response, filed Oct. 7, 2019, to Communication Pursuant to Article 94(3) EPC, dated Jun. 27, 2019, in connection with European Patent Application No. 15852615.2, 20 pages.

Examination Report, dated Jul. 30, 2019, in connection with European Patent Application No. 16754618.3, 9 pages.

Response, filed Feb. 6, 2020, to Examination Report, dated Jul. 30, 2019, in connection with European Patent Application No. 16754618.3, 15 pages.

Office Action, dated Dec. 3, 2019, in connection with Japanese Patent Application No. 2018-507579 [English translation and original document in Japanese], 7 pages.

Response, filed Oct. 3, 2019, to Office Action, dated Jul. 1, 2019, in connection with Israel Application No. 251890 [English translation and English claims and original document as-filed in Hebrew], 14 pages.

Response, filed Sep. 29, 2019, to Examination Report, dated Apr. 18, 2019, in connection with New Zealand Patent Application No. 732211, 54 pages.

Response, filed Jan. 29, 2020, to Examination Report, dated Oct. 31, 2019, in connection with New Zealand Patent Application No. 732211, 10 pages.

Examination Report (claims accepted), dated Feb. 5, 2020, in connection with New Zealand Patent Application No. 732211, 1 page.

Response, filed Oct. 11, 2019, to Official Action, dated May 24, 2019, in connection with Russian Application No. 2017117889 [English instructions, and Response and claims as-filed, in Russian], 74 pages.

Response, filed Oct. 3, 2019, to Written Opinion, dated May 9, 2019, in connection with Singaporean Patent Application No. 11201703326S, 47 pages.

Response, filed Sep. 23, 2019, to Search Report and Written Opinion, dated Apr. 23, 2019, in connection with Singapore Patent Application No. 11201801177T, 47 pages.

U.S. Appl. No. 16/676,413, filed Nov. 6, 2019, 2020/0140824, May 7, 2020.

Letter/Written Disclosure of the Supplemental Information Disclosure Statement for the above-referenced application, filed herewith on Jan. 6, 2021, 2 pages.

Kilinc et al., "Colonization of xenograft tumors by oncolytic vaccinia virus (VACV) results in enhanced tumor killing due to the involvement of myeloid cells," J. Transl. Med. 14(1):340 (2016), 12 pages.

Payne et al., "Human adipose-derived mesenchymal stem cells engineered to secrete IL-10 inhibit APC function and limit CNS autoimmunity," Brain Behavior and Immunity 30(1):103-114 (2013).

Petrov et al., "Canine Adipose-Derived Mesenchymal Stem Cells (cAdMSCs) as a "Trojan Horse" in Vaccinia Virus Mediated Oncolytic Therapy against Canine Soft Tissue Sarcomas," Viruses 12(7):750 (2020), 13 pages.

Rogers et al., "Rationale for the clinical use of adipose-derived mesenchymal stem cells for COVID-19 patients," J. Transl. Med. 18(1):203 (2020), 19 pages.

Verardi et al., "A vaccinia virus renaissance: New vaccine and immunotherapeutic uses after smallpox eradication," Human Vaccines & Immunotherapies 8(7):961-970 (2012).

Wang et al., "Optical detection and virotherapy of live metastatic tumor cells in body fluids with vaccinia strains," PLoS One 8(9):e71105 (2013), 12 pages.

Draganov et al., "Evaluation of the potential of oncolytic vaccinia virus delivered by autologous SVF to modulate innate and adaptive immunity in patients with diverse solid and hematological malignancies," Abstract No. 4473; presented at the AACR Virtual Meeting, held on Jun. 22, 2020, 2 pages.

Nguyen et al., "A cell-based platform to potentiate oncolytic virus therapies," poster presented at ASCO-SITC Clinical Immuno-Oncology Symposium, Feb. 6-8, 2020, Orlando, Florida, 1 page.

Nguyen et al., "A cell-based platform to potentiate oncolytic virus: Potential approach for cancer therapies." Abstract No. 21, presented at the ASCO-SITC Clinical Immuno-Oncology Symposium on Feb. 6, 2020, in Orlando, Florida, 2 pages.

Nguyen et al., "CAL1 vaccinia virus as oncolytic agent and potential use of cell-based platform to enhance its therapeutic effects," Abstract No. 6542; presented at the AACR Virtual Meeting, held on Jun. 22, 2020, 2 pages.

News Release, entitled "Calidi Biotherapeutics Presents Data at the 2020 ASCO-SITC Clinical Immuno-Oncology Symposium," Published Feb. 13, 2020 [online]; Retrieved on Mar. 11, 2020, from: <URL: calidibio.com/2020/02/13/calidi-biotherapeutics-presents-data-at-the-2020-asco-sitc-clinical-immuno-oncology-symposium/, 4 pages.

News Release, entitled "Calidi Biotherapeutics Announces Two Abstracts Accepted for Presentation at AACR 2020 Virtual Annual Meeting II," Published Jun. 22, 2020 [online]; Retrieved on Jun. 23, 2020, from: <URL: businesswire.com/news/home/20200622005121/en/Calidi-Biotherapeutics-Announces-Abstracts-Accepted-Presentation-AACR, 2 pages.

International Search Report and Written Opinion, dated Mar. 9, 2020, in connection with International Patent Application No. PCT/US2019/035464, 40 pages.

Response, filed Jun. 9, 2020, to International Search Report and Written Opinion, dated Mar. 9, 2020, in connection with International Patent Application No. PCT/US2019/035464, 74 pages.

Written Opinion, dated Jul. 3, 2020, in connection with International Patent Application No. PCT/US2019/035464, 10 pages.

Response, filed Sep. 3, 2020, to Written Opinion, dated Jul. 3, 2020, in connection with International Patent Application No. PCT/US2019/035464, 42 pages.

International Preliminary Report on Patentability, dated Sep. 28, 2020, in connection with International Patent Application No. PCT/US2019/035464, 10 pages.

Response, filed Mar. 10, 2020, to Examiner's Report, dated Oct. 25, 2019, in connection with Australian Patent Application No. 2015335607, 19 pages.

Examiner's Report, dated Mar. 12, 2020, in connection with Australian Patent Application No. 2015335607, 5 pages.

Response, filed Mar. 26, 2020, to Examiner's Report, dated Mar. 12, 2020, in connection with Australian Patent Application No. 2015335607, 18 pages.

Notice of Acceptance, dated Apr. 8, 2020, in connection with Australian Patent Application No. 2015335607, 3 pages.

(56) References Cited

OTHER PUBLICATIONS

Preliminary Office Action, dated Oct. 2, 2020, in connection with corresponding Brazilian Patent Application No. BR112017008399-0 [English translation and original document in Portuguese], 6 pages.
Notice of Allowance, dated Apr. 9, 2020, in connection with corresponding Canadian Patent Application No. 3,003,133, 1 page.
Response, filed Apr. 17, 2020, to Communication Pursuant to Article 94(3) EPC (Examination Report), dated Jan. 7, 2020, in connection with corresponding European Patent Application No. 15852615.2, 46 pages.
Communication Pursuant to Rule 71(3) EPC (Intention to Grant), dated Jun. 12, 2020, in connection with corresponding European Patent Application No. 15852615.2, 7 pages.
Notice of Acceptance, dated Apr. 20, 2020, in connection with corresponding New Zealand Patent Application No. 732211, 1 page.
Examination Report, dated Oct. 28, 2020, and Notice of Eligibility for Grant, dated Oct. 29, 2020, in connection with corresponding Singaporean Patent Application No. 11201703326S, 6 pages.
Certificate of Grant, dated Dec. 24, 2020, in connection with corresponding Singaporean Patent Application No. 11201703326S, 1 page.
Examination Report, dated Jul. 29, 2020, in connection with European Patent Application No. 16754618.3, 5 pages.
Response, filed Dec. 3, 2020, to Examination Report, dated Jul. 29, 2020, in connection with European Patent Application No. 16754618.3, 80 pages.
Examination Report [claims deemed allowable], dated Jul. 6, 2020, in connection with Singapore Patent Application No. 11201801177T, 4 pages.
Notice of Eligibility for Grant, dated Jul. 13, 2020, in connection with Singapore Patent Application No. 11201801177T, 1 page.
Letter/Written Disclosure of the Supplemental Information Disclosure Statement for the above-referenced application, filed herewith on Oct. 6, 2021, 2 pages.
News Release, entitled "Calidi Biotherapeutics Announces Partnership with GenScript ProBio for Distribution of its SuperNova-1 Technology." Published Jun. 8, 2021 [online]; retrieved on Jun. 16, 2021, from: <URL:businesswire.com/news/home/20210608005504/en/Calidi-Biotherapeutics-Announces-Partnership-with-GenScript-ProBio-for-Distribution-of-its-SuperNova-1-Technology, 2 pages.
News Release, entitled "Calidi Biotherapeutics Announces Agreement with Northwestern University for Exclusive Commercial Rights to their IND for Treatment of Malignant Glioma." Published Aug. 4, 2021 [online]; retrieved on Oct. 6, 2021, from: <URL:calidibio.com/2021/08/04/calidi-biotherapeutics-announces-agreement-with-northwestern-university-for-exclusive-commercial-rights-to-their-ind-for-treatment-of-malignant-glioma, 4 pages.
News Release, entitled "Calidi Biotherapeutics Announces Exclusive License Agreement with City of Hope and the University of Chicago for Novel Oncolytic Virotherapy Technology." Published Aug. 16, 2021 [online]; retrieved on Oct. 6, 2021, from: <URL:calidibio.com/2021/08/16/calidi-biotherapeutics-announces-exclusive-license-agreement-with-city-of-hope-and-the-university-of-chicago-for-novel-oncolytic-virotherapy-technology, 5 pages.
Examiner's Report, dated Apr. 28, 2021, in connection with related Canadian Patent Application No. 3,100,046, 7 pages.
Response, filed Aug. 30, 2021, to Examiner's Report, dated Apr. 28, 2021, in connection with Canadian Patent Application No. 3,100,046, 128 pages.
Response, filed Jan. 8, 2021, to Preliminary Office Action, dated Oct. 2, 2020, in connection with corresponding Brazilian Patent Application No. BR 112017008399-0 [English language instructions; original document as filed in Portuguese; and Declaration of Dr. Minev in English], 125 pages.
Certificate of Grant, dated Nov. 25, 2020, in connection with corresponding European Patent Application No. 15852615.2, 1 page.
Office Action, dated Jan. 22, 2021, issued in connection with corresponding Mexican Patent Application No. MX/a/2017/005325 [English translation, and original document in Spanish], 8 pages.
Response, filed Mar. 19, 2021, to Office Action, dated Jan. 22. 2021, issued in connection with corresponding Mexican Patent Application No. MX/a/2017/005325 [English instructions for Response; and original Response as filed in Spanish], 33 pages.
Office Action, dated Jun. 2, 2021, issued in connection with corresponding Mexican Patent Application No. MX/a/2017/005325 [English translation, and original document in Spanish], 8 pages.
Notice of Acceptance, dated Jun. 14, 2021, in connection with corresponding South African Patent Application No. 2017/03585, 1 page.
Office Action, dated Jan. 4, 2021, in connection with related Chinese Patent Application No. 201680058874.X [English translation, and original document as issued in Chinese], 12 pages.
Response, filed May 19, 2021, to Office Action, dated Jan. 4, 2021, in connection with related Chinese Patent Application No. 201680058874.X [English language instructions for response; original documents as filed in Chinese; and English translation of amended claims], 28 pages.
Office Action, dated Feb. 4, 2021, issued in connection with related Eurasian Patent Application No. 201800148 [Reporting letter, dated Feb. 17, 2021, providing an English translation of the Office Action; and original Office Action as issued in Russian], 4 pages.
Response, filed Aug. 13, 2021, to Office Action, dated Feb. 4, 2021, issued in connection with Eurasian Patent Application No. 201800148 [English Instructions for Response, Response as filed in Russian], 25 pages.

\* cited by examiner

| Problem | Solution |
| --- | --- |
| Immunosuppressive tumor microenvironment | Sensitization (e.g., with local tumor irradiation and other means) converts tumor microenvironment into an immunogenic one |
| Intratumoral inactivation of payload delivery system by the immune system | Intratumoral injection of protective stem cells with payload prevents inactivation |
| Intratumoral inactivation of the released payload by the immune system | Precise transient inactivation of specific host immune components ensures long-lasting payload presence |
| Inefficient tumor cell lysis | Efficient stem cell-based payload delivery, extended payload presence, tumor cell killing |
| Inefficient targeting of cancer stem cells | Efficient payload delivery simultaneously eliminates tumor cells and cancer stem cells (CSC's) |
| Inefficient T-cell induction and limited expansion | Checkpoint inhibition and growth factor release leading to efficient T-cell activation and significant expansion |

COMBINATION IMMUNOTHERAPY APPROACH FOR TREATMENT OF CANCER

CROSS-REFERENCE TO RELATED APPLICATIONS

This application is a U.S. National Stage Application filed under 35 U.S.C. § 371 and claims priority to International Application No. PCT/US2015/057234 filed on Oct. 23, 2015, which claims benefit of priority to U.S. Provisional Application No. 62/068,557, filed Oct. 24, 2014, U.S. Provisional Application No. 62/073,907, filed Oct. 31, 2014, the disclosures of which are incorporated herein by reference in their entireties.

BACKGROUND OF THE INVENTION

Cancer is the second most common cause of death in the United States, exceeded only by heart disease. In the United States, cancer accounts for 1 of every 4 deaths. The 5-year relative survival rate for all cancer patients diagnosed in 1996-2003 is 66%, up from 50% in 1975-1977 (Cancer Facts & Figures American Cancer Society: Atlanta, Ga. (2008)). Discovering highly effective cancer treatments is a primary goal of cancer research.

The tumor stem cell hypothesis may explain the resistance of some tumors to conventional therapies. In this model, a certain subset of tumor cells, with characteristics similar to some stem cells, is capable of producing a variety of cell types, which constitute the bulk of the tumor. An effective approach for eradicating these cells is needed.

SUMMARY OF THE INVENTION

The present invention relates generally to the treatment of human cancer and, more specifically, to use of several treatment modalities in combination to induce effective anti-tumor immune responses.

Disclosed herein, in some embodiments, is a method for treating a solid tumor or hematologic malignancy in a subject, comprising two or more of the following: (a) sensitizing a tumor by administering to the subject a treatment that will: (i) induce apoptosis in cells within the tumor, (ii) modify the tumor environment, (iii) stimulate tumor-infiltrating immune cells, or (iv) a combination thereof; (b) injecting into the subject: (i) a modified stem cell, wherein the modified stem cell comprises a cytotoxic payload; (ii) a wild-type or genetically modified virus; (iii) a wild-type or genetically modified bacteria; or (iv) a combination thereof; and (c) administering a treatment to the subject that will activate the T-cell response within the subject. In some embodiments, step (a) is performed before step (b) and step (c). In some embodiments, step (b) is performed after step (c). In some embodiments, step (b) is performed before step (c). In some embodiments, any of the steps are performed concurrently.

In some embodiments, the treatment that will induce apoptosis in cells within the tumor is selected from the group consisting of: radiation therapy, chemotherapy, immunotherapy, phototherapy, or a combination thereof. In some embodiments, the treatment that will induce apoptosis in cells is immunotherapy. In some embodiments, the immunotherapy is selected from peptide vaccine therapy using tumor antigen peptides; adoptive immunotherapy using lymphocytes such as cytotoxic T cells or natural killer cells; DNA vaccine therapy which involves administration of organisms comprising vectors expressing tumor antigen proteins or tumor antigen peptides; and dendritic cell vaccine therapy which involves administering dendritic cells displaying tumor antigen peptides. In some embodiments, the treatment that will induce apoptosis in cells is chemotherapy. In some embodiments, the chemotherapy comprises administration of a chemotherapeutic agent is selected from an alkylating drug, an antimetabolite, an antimytotic cytostatic, a topoisomerase inhibitor, antitumor antibiotic, and any other cytostatic, and/or a radiotherapy. In some embodiments, the chemotherapeutic agent is an alkylating agent. In some embodiments, the alkylating agent is selected from cisplatin, oxaliplatin, cyclop hosphamid, ifosfamid, trofosfamid, melphalan, chlorambucil, estramustin, busulfan, treosulfan, carmustin, lomustin, nimustin, streptozocin, procarbazin, dacarbazin, temozolomid, and thiotepa. In some embodiments, the chemotherapeutic agent is an antimetabolite. In some embodiments, the antimetabolite is selected from 5-fluorouracil, methotrexate, azacitidin, capecitabin, doxifluridin, cytarabin, gemcitabin, 6-thioguanin, pentostatin, azathioprin, 6-mercaptopurin, fludarabin, and cladribin. In some embodiments, the chemotherapeutic agent is a topoisomerase inhibitor. In some embodiments, the topoisomerase inhibitor is selected from doxorubicin, camptothecin, topotecan, irinotecan, etoposide, and teniposide. In some embodiments, the chemotherapeutic agent is an antitumor antibiotic. In some embodiments, the antitumor antibiotic is selected from tamoxifen, 5-fluoro-5'-deoxyuridine, belomycin, actinomycin D, and mitomycin. In some embodiments, the chemotherapeutic agent is a cytostatic. In some embodiments, the cytostatic is L-asparaginase or hydroxycarb amide. In some embodiments, the treatment that will induce apoptosis in cells is phototherapy. In some embodiments, the phototherapy is selected from ultraviolet B radiation (UVB) phototherapy and ultraviolet A photochemotherapy (PUVA). In some embodiments, the phototherapy further comprises the use of psoralen. In some embodiments, sensitizing the tumor comprises administering irradiation to the subject. In some embodiments, the irradiation is ionizing radiation. In some embodiments, the irradiation is high-dose hypofractionation radiation therapy (HDHRT). In some embodiments, step (a) comprises modification of the tumor microenvironment. In some embodiments, modification of the tumor microenvironment comprises administration of a cytokine-blocking agent. In some embodiments, the cytokine-blocking agent is selected from Ustekinumab, Adalimumab, Infliximab, Etanercept, and Golimumab.

In some embodiments, step (b) comprises injecting into the subject a modified stem cell, wherein the modified stem cell comprises a cytotoxic payload. In some embodiments, the modified stem cell carries one or more imaging payloads. In some embodiments, the modified stem cell carries one or more of a virus, an antibody, or a cytokine as the cytotoxic payload. In some embodiments, the modified stem cell expresses a cytokine as the cytotoxic payload. In some embodiments, the cytokine is selected from colony-stimulating factor (CSF), interferon (IFN), interleukin (IL), stem cell factor (SCF), tumour growth factors (TGF), and tumour necrosis factor (TNF). In some embodiments, the cytokine is a CSF. In some embodiments, the CSF is G-CSF, M-CSF, or GM-CSF. In some embodiments, the CSF is selected from ancestim, garnocestim, pegacaristim, leridistim, milodistim, filgrastim, lenograstim, nartograstim, pegfilgrastim, pegnartograstim, ecogramostim, molgramostim, regramostim, sargramostim, cilmostim, lanimostim, mirimostim, daniplestim, muplestim, or derivates thereof. In some embodiments, the cytokine is an interleukin (IL). In some embodiments, the interleukin is selected from IL-1 to IL-35, and derivates thereof. In some embodiments, the interleukin is IL-2, IL-4, or derivates thereof. In some embodiments, the cytotoxic payload comprises a lytic virus. In some embodiments, the lytic virus is a vaccinia virus. In some embodiments, the cytotoxic payload comprises a chemotherapeutic agent. In some embodiments, step (b) results in in situ vaccination of the subject against the tumor.

In some embodiments, the modified stem cell is an adult stem cell. In some embodiments, the modified stem cell is transformed with a lenti-virus or retrovirus. In some embodiments, the modified stem cell is transiently transfected with an artificial chromosome, virus or plasmid DNA. In some embodiments, the modified stem cell is capable of localizing to the tumor. In some embodiments, the modified stem cell is autologous. In some embodiments, the modified stem cell is allogeneic. In some embodiments, the modified stem cell is selected from the group consisting of adult stem cells, embryonic stem cells, fetal stem cells, mesenchymal stem cells, neural stem cells, totipotent stem cells, pluripotent stem cells, multipotent stem cells, oligopotent stem cells, unipotent stem cells, adipose stromal cells, endothelial stem cells, and combinations thereof. In some embodiments, the modified cell is derived from adipose-derived Stromal Vascular Fraction (SVF), which comprises adult stem cells, monocytes/macrophages, regulatory T cells, endothelial cells, and combinations thereof. In some embodiments, the modified stem cell is injected into the subject in conjunction with adipose-derived SVF. In some embodiments, the modified stem cell is an umbilical cord-derived mesenchymal like cell. In some embodiments, the umbilical cord-derived mesenchymal-like cell is an Immstem™ cell.

In some embodiments, step (b) further comprises treatment of the modified stem cell with a treatment selected from: a TLR agonist; intravenous immunoglobulin (IVIG); monocyte conditioned media; supernatant from neutrophil extracellular trap-exposed peripheral blood mononuclear cells; co-culture with monocytes; co-culture with monocytes that have been pretreated with IVIG; co-culture with T cells; coculture with T cells that have been exposed to a T cell stimulus; co-culture with natural killer cells; peptidoglycan isolated from gram positive bacteria; lipoarabinomannan isolated from mycobacteria; zymosan isolated from a yeast cell wall; polyadenylic-polyuridylic acid; poly (IC); lipopolysaccharide; monophosphoryl lipid A; flagellin; Gardiquimod; Imiquimod; R848; oligonucleosides containing CpG motifs; and 23S ribosomal RNA.

In some embodiments, step (c) comprises injection of a stem cell into the subject. In some embodiments, the stem cell is an adult stem cell. In some embodiments, the stem cell is capable of excreting growth factors. In some embodiments, the stem cell is injected into the site of the tumor. In some embodiments, the stem cell is injected into the tumor. In some embodiments, the stem cell produces antibodies, or growth factors capable of stimulating T-cell growth and expansion. In some embodiments, the stem cell is transformed with a lenti-virus or retrovirus. In some embodiments, the lenti-virus or retrovirus comprise a heterologous nucleic acid encoding a protein involved in T-cell activation. In some embodiments, the stem cell is transiently transfected with an artificial chromosome, virus or plasmid DNA.

In some embodiments, step (c) comprises promoting simultaneous signaling through the T cell receptor and a costimulatory molecule. In some embodiments, the costimulatory molecule is CD28.

In some embodiments, step (c) comprises administering to the tumor one or more T-cells expressing one or more growth factors.

In some embodiments, step (c) comprises administering agonistic antibodies directed against activating co-stimulatory molecules. In some embodiments, step (c) comprises administration of agonistic antibodies against a co-stimulatory molecule selected from the group consisting of: CD28, OX40, GITR, CD137, CD27 and HVEM.

In some embodiments, step (c) comprises administering blocking antibodies against negative co-stimulatory molecules. In some embodiments, step (c) comprises administration of blocking antibodies against a negative co-stimulatory molecule selected from the group consisting of: CTLA-1; PD-1, TIM-3, BTLA, VISTA and LAG-3. In some embodiments, step (c) comprises administration of CTLA-4 blocking antibodies. In some embodiments, step (c) comprises administration of inhibitors of the PD-1 pathway. In some embodiments, the inhibitor of the PD-1 pathway is selected from antibodies against PD-1 and soluble PD-1 ligand. In some embodiments, the inhibitors of the PD-1 pathway are selected from AMP-244, MEDI-4736, MPDL328 OA, and MIH1.

In some embodiments, the tumor is selected from: glioblastoma, breast carcinoma, lung carcinoma, prostate carcinoma, colon carcinoma, ovarian carcinoma, neuroblastoma, central nervous system tumor, melanoma, and hematologic malignancies.

BRIEF DESCRIPTION OF THE DRAWINGS

FIG. 1 exemplifies a non-limiting embodiment of a method for combination immunotherapy of cancer, composed of three elements: Sensitization of tumor sites; In situ vaccination or immunization utilizing patient's own tumor cells; T-cell induction [S.I.T.]. In the exemplified embodiment, tumor sensitization is accomplished via irradiation (Step 1) although any other suitable sensitization methodology can be utilized, in situ vaccination or immunization is induced by injecting into the tumor healthy stem cells armed with a cytotoxic payload (Step 2), immune checkpoint inhibitors, growth factor inhibitors, etc., can be administered (e.g., simultaneously) as well (Step 2+3), and to induce T-cell activation, the tumor is injected with healthy stem cells containing growth factors which produces a long-lasting anti-tumor and clinical response (Step 3).

DETAILED DESCRIPTION OF THE PREFERRED EMBODIMENTS

A tumor's escape from immune control (immune evasion) is being increasingly recognized as a vital capability allowing tumor expansion and clinical presentation. Immune evasion mechanisms include antigenic loss, downregulation of MHC molecules, secretion of immune-suppressive cytokines, recruitment of regulatory, tolerogenic and suppressive innate and adaptive immune cells and upregulation of immuno-suppressive receptors, among others. In addition, the paucity of endothelial adhesion molecules in tumor vasculature and abnormal architecture presents significant barriers to T cell infiltration into tumors. Therefore, the tumor microenvironment actively supports tumor growth and prevents tumor rejection.

Converting the immunosuppressive tumor microenvironment into an immunogenic environment can be a successful immuno-therapeutic strategy against cancer.

Figure 1:
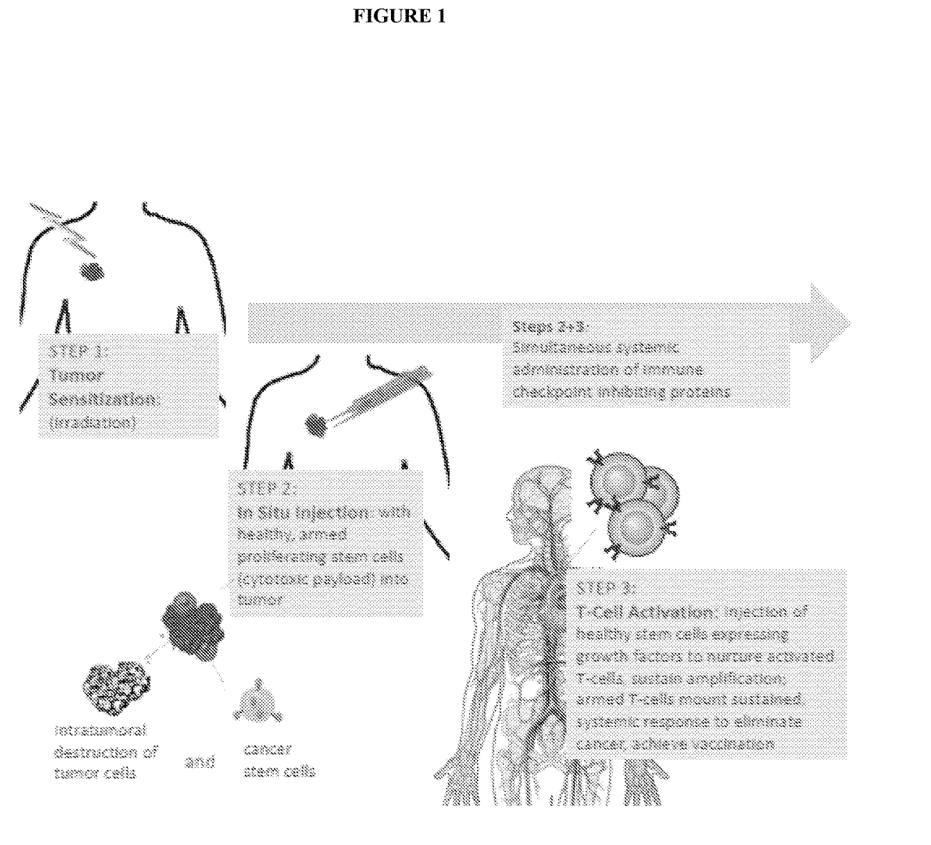
Figure 2:
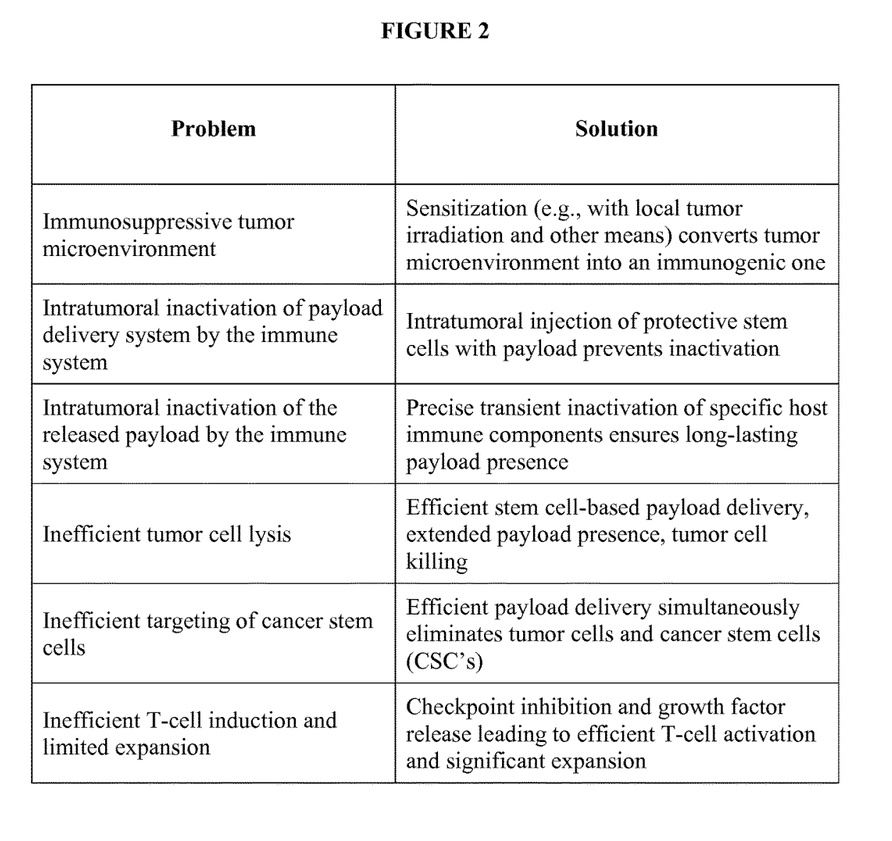
FIG. 2. illustrates non-limiting examples of how one or more embodiments of the present technology can overcome various challenges associated with other approaches to targeting cancer.

Many of the embodiments described herein are able to overcome one or more of the challenges or limitations typically associated with other approaches to targeting cancer (See FIG. 2). For example, sensitization converts a normally immuno-suppressive tumor microenvironment into an immunogenic one. Additionally, an intratumoral injection of armed protective stem cells (payload delivery) prevents the immune system from inactivating the payload. Such a precise transient inactivation of specific host immune components ensures a long-lasting payload presence which is capable of simultaneously killing both tumor cells and cancer stem cells whereas other approaches are limited by inefficient tumor cell lysis and inefficient targeting of cancer stem cells. Finally, checkpoint inhibition and growth factor release leads to an efficient T-cell activation and significant expansion whereas other approaches are hindered by inefficient T-cell induction and limited expansion.

Accordingly, embodiments of the present invention generally relate to methods for the treatment of human cancer and, more specifically, in some embodiments to the use of multiple treatment modalities in combination to induce effective anti-tumor immune response.

Definitions

As used herein, a subject includes any animal for which diagnosis, screening, monitoring or treatment is contemplated. Animals include mammals such as primates and domesticated animals. An exemplary primate is human. A patient refers to a subject such as a mammal, primate, human, or livestock subject afflicted with a disease condition or for which a disease condition is to be determined or risk of a disease condition is to be determined.

As used here, the term "antibody" is used in the broadest sense and specifically covers monoclonal antibodies (including full length monoclonal antibodies), polyclonal antibodies, multispecific antibodies (e.g., bispecific antibodies), bi-specific T cell engagers (BiTE) antibodies, and antibody fragments (e.g., single-chain, nanobodies, etc.) so long as they exhibit the desired biological activity.

As used herein, "virus" refers to any of a large group of entities referred to as viruses. Viruses typically contain a protein coat surrounding an RNA or DNA core of genetic material, but no semipermeable membrane, and are capable of growth and multiplication only in living cells. Viruses for use in the methods provided herein include, but are not limited, to a poxvirus, adenovirus, herpes simplex virus, Newcastle disease virus, vesicular stomatitis virus, mumps virus, influenza virus, measles virus, reovirus, human immunodeficiency virus (HIV), hanta virus, myxoma virus, cytomegalovirus (CMV), lentivirus, and any plant or insect virus.

As used herein, the term "viral vector" is used according to its art-recognized meaning. It refers to a nucleic acid vector construct that includes at least one element of viral origin and can be packaged into a viral vector particle. The viral vector particles can be used for the purpose of transferring DNA, RNA or other nucleic acids into cells either in vitro or in vivo. Viral vectors include, but are not limited to, retroviral vectors, vaccinia vectors, lentiviral vectors, herpes virus vectors (e.g., HSV), baculoviral vectors, cytomegalovirus (CMV) vectors, papillomavirus vectors, simian virus (SV40) vectors, semliki forest virus vectors, phage vectors, adenoviral vectors, and adeno-associated viral (AAV) vectors.

As used herein, "hematologic malignancy" refers to tumors of the blood and lymphatic system (e.g. Hodgkin's disease, Non-Hodgkin's lymphoma, Burkitt's lymphoma, AIDS-related lymphomas, malignant immunoproliferative diseases, multiple myeloma and malignant plasma cell neoplasms, lymphoid leukemia, myeloid leukemia, acute or chronic lymphocytic leukemia, monocytic leukemia, other leukemias of specified cell type, leukemia of unspecified cell type, other and unspecified malignant neoplasms of lymphoid, haematopoietic and related tissues, for example diffuse large cell lymphoma, T-cell lymphoma or cutaneous T-cell lymphoma).

Combination Immunotherapy

In one aspect, the invention provides a strategy for combination immunotherapy of cancer, composed of at least three elements: Sensitization of tumor sites; In situ vaccination utilizing patient's own tumor cells; T-cell induction (S.I.T. Technology). It should be understood that the elements can be utilized individually, in a two-element combination, and with other treatments and modalities, as well according to some embodiments. In one embodiment, the invention provides methods to sensitize tumor sites in preparation for the subsequent treatment elements. In another embodiment, the invention provides methods for killing tumor cells for in situ vaccination. In yet another embodiment, the invention provides methods for designing vehicles for delivery of tumor cell-killing agents ("Trojan Horse" delivery technology). In yet another embodiment, the invention provides methods for induction and expansion of tumor-specific T cells. Such methods can be used together or in any combination. One or more of the described methods can be specifically excluded from some embodiments.

Growing evidence supports the notion that personalized immunotherapy utilizing multiple antigens and treatment approaches will lead to effective tumor targeting. Importantly, in situ vaccinations with patient's own killed tumor cells will provide the entire antigenic diversity of patient's own tumor. This approach, when combined with other immunotherapeutic strategies, will induce broad, long-lasting and potent anti-tumor immune responses that will lead to the eradication of both treated tumors, as well as non-treated distant metastatic tumor deposits.

The methods disclosed herein can be used to treat any solid tumor or hematologic malignancy. Tumors that can be treated by the methods disclosed herein include, but are not limited to a bladder tumor, breast tumor, prostate tumor, carcinoma, basal cell carcinoma, biliary tract cancer, bladder cancer, bone cancer, brain cancer, CNS cancer, glioma tumor, cervical cancer, choriocarcinoma, colon and rectum cancer, connective tissue cancer, cancer of the digestive system, endometrial cancer, esophageal cancer, eye cancer, cancer of the head and neck, gastric cancer, intra-epithelial neoplasm, kidney cancer, larynx cancer, leukemia, liver cancer, lung cancer, lymphoma, Hodgkin's lymphoma, Non-Hodgkin's lymphoma, melanoma, myeloma, neuroblastoma, oral cavity cancer, ovarian cancer, pancreatic cancer, retinoblastoma, rhabdomyosarcoma, rectal cancer, renal cancer, cancer of the respiratory system, sarcoma, skin cancer, stomach cancer, testicular cancer, thyroid cancer, uterine cancer, and cancer of the urinary system, such as lymphosarcoma, osteosarcoma, mammary tumors, mastocytoma, brain tumor, melanoma, adenosquamous carcinoma, carcinoid lung tumor, bronchial gland tumor, bronchiolar adenocarcinoma, small cell lung cancer, non-small cell lung cancers, fibroma, myxochondroma, pulmonary sarcoma, neurosarcoma, osteoma, papilloma, retinoblastoma, Ewing's sarcoma, Wilm's tumor, Burkitt's lymphoma, microglioma, neuroblastoma, osteoclastoma, oral neoplasia, fibrosarcoma, osteosarcoma and rhabdomyosarcoma, genital squamous cell carcinoma, transmissible venereal tumor, testicular tumor, seminoma, Sertoli cell tumor, hemangiopericytoma, histiocytoma, chloroma, granulocytic sarcoma, corneal papilloma, corneal squamous cell carcinoma, hemangiosarcoma, pleural mesothelioma, basal cell tumor, thymoma, stomach tumor, adrenal gland carcinoma, oral papillomatosis, hemangioendothelioma, cystadenoma, follicular lymphoma, intestinal lymphosarcoma, fibrosarcoma, and pulmonary squamous cell carcinoma, leukemia, hemangiopericytoma, ocular neoplasia, preputial fibrosarcoma, ulcerative squamous cell carcinoma, preputial carcinoma, connective tissue neoplasia, mastocytoma, hepatocellular carcinoma, lymphoma, pulmonary adenomatosis, pulmonary sarcoma, Rous sarcoma, reticulo-endotheliosis, fibrosarcoma, nephroblastoma, B-cell lymphoma, lymphoid leukosis, retinoblastoma, hepatic neoplasia, lymphosarcoma, plasmacytoid leukemia, swimbladder sarcoma (in fish), caseous lumphadenitis, lung carcinoma, insulinoma, lymphoma, sarcoma, neuroma, pancreatic islet cell tumor, gastric MALT lymphoma and gastric adenocarcinoma. In some embodiments, the tumor is selected from: glioblastoma, breast carcinoma, lung carcinoma, prostate carcinoma, colon carcinoma, ovarian carcinoma, neuroblastoma, central nervous system tumor, and melanoma.

Tumor Sensitization

Disclosed herein in some embodiments, is a method of sensitizing a tumor to subsequent treatment modalities. The sensitization portion of the technology according to some embodiments may be performed using any of the approaches described herein. In some embodiments, a tumor is sensitized by administering to a subject a treatment that will: (i) induce apoptosis in cells within the tumor, (ii) modify the tumor environment, (iii) stimulate tumor-infiltrating immune cells, or (iv) a combination of two or more thereof.

In some embodiments, the treatment that will induce apoptosis in cells within the tumor is selected from the group consisting of: radiation therapy, chemotherapy, immunotherapy, phototherapy, or a combination thereof.

In some embodiments, the treatment that will induce apoptosis in cells is immunotherapy. In some embodiments, the immunotherapy is selected from peptide vaccine therapy using tumor antigen peptides; adoptive immunotherapy using lymphocytes such as cytotoxic T cells or natural killer cells; DNA vaccine therapy which involves administration of organisms comprising vectors expressing tumor antigen proteins or tumor antigen peptides; and dendritic cell vaccine therapy which involves administering dendritic cells displaying tumor antigen peptides.

In some embodiments, the treatment that will induce apoptosis in cells is phototherapy. In some embodiments, the phototherapy is selected from ultraviolet B radiation (UVB) phototherapy and ultraviolet A photochemotherapy (PUVA). In some embodiments, the phototherapy further comprises the use of psoralen.

In some embodiments, sensitizing the tumor comprises administering irradiation to the subject. In some embodiments, the irradiation is ionizing radiation. In one embodiment, the sensitization will be achieved with local tumor irradiation, e.g. high-dose hypofractionation radiation therapy (HDHRT).

Ionizing radiation has a significant potential to modify the tumor microenvironment and facilitate immune-mediated tumor rejection. Specifically, radiation can induce remodeling of the abnormal tumor vessels and up-regulation of vascular cell adhesion molecules (e.g. VCAM-1) and chemokine secretion (e.g. CXCL16), resulting in efficient T-cell infiltration into the tumor. Other important effects of radiation include up-regulation of MHC class-I molecules, NKG2D ligands, and Fas/CD95, thus augmenting T-cell binding to and killing of the cancer cells. However, despite these significant pro-immunogenic effects, radiation by itself is insufficient to induce long-lasting and powerful enough anti-tumor immune responses leading to tumor eradication.

Radiation therapy includes, but is not limited to, photodynamic therapy, radionuclides, radio immunotherapy and proton beam treatment.

In some embodiments, the treatment that will induce apoptosis in cells within the tumor comprises administration of a chemotherapeutic compound. Chemotherapeutic compounds include, but are not limited to platinum; platinum analogs (e.g., platinum coordination complexes) such as cisplatin, carboplatin, oxaliplatin, DWA2114R, NK121, IS 3 295, and 254-S; anthracenediones; vinblastine; alkylating agents such as thiotepa and cyclosphosphamide; alkyl sulfonates such as busulfan, improsulfan and piposulfan; aziridines such as benzodopa, carboquone, meturedopa and uredopa; ethylenimines and methylamelamines including altretamine, triethylenemelamine, trietylenephosphoramide, triethylenethiophosphaoramide and trimethylolomelamime nitrogen mustards such as chiorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; substituted ureas; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; anti-cancer polysaccharides; polysaccharide-K; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; cytosine arabinoside; cyclophosphamide; thiotepa; taxoids, such as paclitaxel and doxetaxel; chlorambucil; gemcitabine; 6-thioguanine; mercaptopurine; methotrexate; etoposide (VP-16); ifosfamide; mitomycin C; mitoxantrone;

vincristine; vinorelbine; navelbine; novantrone; teniposide; daunomycin; aminopterin; XELODA; ibandronate; CPT11; topoisomerase inhibitor RFS 2000; difluoromethylornithine (DMFO); retinoic acid; esperamicins; capecitabine; methylhydrazine derivatives; Erlotinib (TARCEVA); sunitinib malate (SUTENT); and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone and toremifene (FARESTON); adrenocortical suppressants; and antiandrogens such as flutamide, nilutamide, bicalutamide, leuprolide and goserelin; and pharmaceutically acceptable salts, acids or derivatives of any of the above. Such chemotherapeutic compounds that can be used herein include compounds whose toxicities preclude use of the compound in general systemic chemotherapeutic methods. In some embodiments, the chemotherapy comprises administration of a chemotherapeutic agent is selected from an alkylating drug, an antimetabolite, an antimyotic cytostatic, a topoisomerase inhibitor, antitumor antibiotic, and any other cytostatic, and/or a radiotherapy. In some embodiments, the chemotherapeutic agent is an alkylating agent. In some embodiments, the alkylating agent is selected from cisplatin, oxaliplatin, cyclop hosphamid, ifosfamid, trofosfamid, melphalan, chlorambucil, estramustin, busulfan, treosulfan, carmustin, lomustin, nimustin, streptozocin, procarbazin, dacarbazin, temozolomid, and thiotepa. In some embodiments, the chemotherapeutic agent is an antimetabolite. In some embodiments, the antimetabolite is selected from 5-fluorouracil, methotrexate, azacitidin, capecitabin, doxifluridin, cytarabin, gemcitabin, 6-thioguanin, pentostatin, azathioprin, 6-mercaptopurin, fludarabin, and cladribin. In some embodiments, the chemotherapeutic agent is a topoisomerase inhibitor. In some embodiments, the topoisomerase inhibitor is selected from doxorubicin, camptothecin, topotecan, irinotecan, etoposide, and teniposide. In some embodiments, the chemotherapeutic agent is an antitumor antibiotic. In some embodiments, the antitumor antibiotic is selected from tamoxifen, 5-fluoro-5'-deoxyuridine, belomycin, actinomycin D, and mitomycin. In some embodiments, the chemotherapeutic agent is a cytostatic. In some embodiments, the cytostatic is L-asparaginase or hydroxycarb amide.

In some embodiments, the tumor microenvironment is modified by a treatment selected from: local tumor irradiation, cytokine injections, cytokine-blocking agents (e.g. Ustekinumab, Adalimumab, Infliximab, Etanercept, Golimumab), antibody injections, and injection of stem cells secreting cytokines and/or chemokines.

In some embodiments, stimulating tumor-infiltrating immune cells in the sensitization phase is accomplished via a treatment selected from: local tumor irradiation, cytokine injections, antibody injections, and injection of stem cells secreting cytokines and/or chemokines.

In Situ Vaccination

Disclosed herein, in some embodiments, is a method of treating a solid tumor comprising administration of a treatment that will result in in situ vaccination of a subject against the tumor by the tumor's own antigens. In some embodiments, the method comprises injecting into the subject: (i) a modified stem cell, wherein the modified stem cell comprises a cytotoxic payload; (ii) a wild-type or genetically modified virus; (iii) a wild-type or genetically modified bacteria; or (iv) a combination of two or more thereof ("Trojan Horse" delivery technology).

The in situ vaccination portion of the invention may be performed using any of the approaches described in the invention, including viruses and specific chemotherapeutic agents used directly, or within adult stem cell delivery vehicles. In some embodiments, the adult stem cells are permanently transformed (e.g. with lenti-virus or retro-virus), or transiently altered with artificial chromosomes, viruses or plasmid DNA, to produce viruses, antibodies, cytokines or other proteins as payloads to kill tumor cells and cancer stem cells.

The immune system has developed precise sensors to distinguish cell death due to physiological tissue turnover from pathogenic cell death. The innate immune cells have an important class of receptors, the pattern recognition receptors (PRR), dedicated to this function. The PRR bind to pathogen-associated molecular pattern (PAMP) molecules derived from infectious agents and damage-associated molecular pattern (DAMP) molecules derived from cells dying a stressful/immunogenic death.

The immunogenic cell death (ICD) inducers (e.g. chemotherapeutics and radiation) and viruses induce a similar danger response, leading to anticancer immunity. ICD induced by radiation and specific chemotherapeutic agents results in reactive oxygen species (ROS) production and an endoplasmic reticulum (ER) stress response. Active infection of tumor cells by viruses overwhelms the cellular machinery, resulting in ER stress and tumor cell death. During these sequences of events, tumor cells express calreticulin (CRT) on the cell surface that attracts antigen-presenting cells (APCs). In addition, dying cells release immunomodulatory molecules such as high-mobility group box 1 (HMGB1) and adenosine triphosphate (ATP) into the extracellular tumor microenvironment, leading to potent antigen presentation. APCs that take up tumor-associated antigens migrate to the lymph nodes to present these antigens to naïve T cells for establishment of anticancer immunity. In addition to danger-associated molecular patterns (DAMPs), virus infected tumor cells release pathogen-associated molecular patterns (PAMPs) (foreign viral proteins and viral DNA/RNA) that are potent activators of innate immune cells to secrete cytokines, such as the type I IFN. These cytokines help orchestrate the anticancer adaptive immune response. Therefore, the ICD constitutes a prominent pathway for the activation of the immune system against cancer, which in turn determines the long-term success of all anticancer therapies.

Development of optimal vehicles for delivery of the ICD inducers to the tumor sites is an essential element of the overall combination immunotherapy strategy. Some ICD inducers, like chemotherapeutic agents and viruses, are subject to significant elimination and/or neutralization following systemic application. Therefore, designing suitable vehicles for their shielding from the elements of the humoral and cellular immunity in the blood stream, as well as methods for their targeted delivery to the tumor sites is of paramount importance. Recent studies have demonstrated extensive homing of stem cells to glioma tumors and the potential of gene loading into stem cells using viral vectors. These studies indicate that the stem cells are a promising candidate as a vehicle for delivery of the ICD inducers to the tumor sites.

Accordingly, in some embodiments, in situ vaccination comprises injecting into the subject a modified stem cell, wherein the modified stem cell comprises a cytotoxic payload ("Trojan Horse" delivery technology). In some embodiments, the modified stem cell carries one or more imaging payloads. In some embodiments, the modified stem cell carries one or more of a virus, an antibody, or a cytokine as the cytotoxic payload. In some embodiments, the modified stem cell expresses a cytokine as the cytotoxic payload. In some embodiments, the cytokine is selected from colony-stimulating factor (CSF), interferon (IFN), interleukin (IL), stem cell factor (SCF), tumour growth factors (TGF), and tumour necrosis factor (TNF). In some embodiments, the cytokine is a CSF. In some embodiments, the CSF is G-CSF, M-CSF, or GM-CSF. In some embodiments, the CSF is selected from ancestim, garnocestim, pegacaristim, leridistim, milodistim, filgrastim, lenograstim, nartograstim, pegfilgrastim, pegnartograstim, ecogramostim, molgramostim, regramostim, sargramostim, cilmostim, lanimostim, mirimostim, daniplestim, muplestim, or derivates thereof. In some embodiments, the cytokine is an interleukin (IL). In some embodiments, the interleukin is selected from IL-1 to IL-35, and derivates thereof. In some embodiments, the interleukin is IL-2, IL-4, or derivates thereof. In some embodiments, the cytotoxic payload comprises a lytic virus. In some embodiments, the lytic virus is a vaccinia virus. In some embodiments, the cytotoxic payload comprises a chemotherapeutic agent. In some embodiments, step (b) results in in situ vaccination of the subject against the tumor.

In some embodiments, the modified stem cell is an adult stem cell. In some embodiments, the modified stem cell is transformed with a lenti-virus or retrovirus. In some embodiments, the modified stem cell is transiently transfected with an artificial chromosome, virus or plasmid DNA. In some embodiments, the modified stem cell is capable of localizing to the tumor. In some embodiments, the modified stem cell is autologous. In some embodiments, the modified stem cell is allogeneic. In some embodiments, the modified stem cell is selected from the group consisting of adult stem cells, embryonic stem cells, fetal stem cells, mesenchymal stem cells, neural stem cells, totipotent stem cells, pluripotent stem cells, multipotent stem cells, oligopotent stem cells, unipotent stem cells, adipose stromal cells, endothelial stem cells, and combinations thereof. In some embodiments, the modified cell is derived from adipose-derived Stromal Vascular Fraction (SVF), comprising adult stem cells, monocytes/macrophages, regulatory T cells, endothelial cells, and combinations thereof. In some embodiments, the modified stem cell is injected into the subject in conjunction with adipose-derived SVF. In some embodiments, the modified stem cell is an umbilical cord-derived mesenchymal like cell. In some embodiments, the umbilical cord-derived mesenchymal-like cell is an Immstem™ cell.

ImmStem are umbilical cord-derived mesenchymal-like cells, which possess pluripotent differentiation capacity and are characterized by unique surface markers and growth factor production. ImmStem possess numerous advantages compared to other stem cell sources, including ease of collection, higher rate of proliferation, very low immunogenicity, and ability to differentiate into tissues representative of all three germ layer components. In comparison to other mesenchymal stem cell (MSC) subtypes, ImmStem has demonstrated upregulated anti-inflammatory and migratory capacity due to a "cytokine priming" step, which is performed prior to administration. ImmStem cells are generated from human umbilical cords, which are obtained from full term women immediately after delivery. To stimulate a stress response, the cells are cultured for 48 hours with interferon gamma.

Other agents may be used within the practice of the current invention to augment immune modulatory, migratory, or growth factor producing activity of said modified stem cell, which include, a) a TLR agonist; b) intravenous immunoglobulin (IVIG); c) monocyte conditioned media; d) supernatant from neutrophil extracellular trap exposed peripheral blood mononuclear cells; e) co-culture with monocytes; f) co-culture with monocytes that have been pretreated with IVIG; g) co-culture with T cells; h) co-culture with T cells that have been exposed to a T cell stimulus; i) co-culture with NK cells; j) peptidoglycan isolated from gram positive bacteria; k) lipoteichoic acid isolated from gram positive bacteria; l) lipoprotein isolated from gram positive bacteria; m) lipoarabinomannan isolated from mycobacteria, n) zymosan isolated from yeast cell well; o) Polyadenylic-polyuridylic acid; p) poly (IC); q) lipopolysaccharide; r) monophosphoryl lipid A; s) flagellin; t) Gardiquimod; u) Imiquimod; v) R848; w) oligonucleosides containing CpG motifs; and x) 23S ribosomal RNA.

In some embodiments, in situ vaccination of the subject against a tumor comprises injecting into the subject a wild-type or genetically modified virus.

In some embodiments, in situ vaccination of the subject against a tumor comprises injecting into the subject a wild-type of genetically modified bacteria.

T-Cell Induction

Disclosed herein, in some embodiments, is the combination of activating the T-cell response within a subject in need thereof in combination with a treatment disclosed herein.

Cytotoxic T lymphocytes (CTL) are among the most direct and effective elements of the immune system that are capable of generating anti-tumor immune responses. Tumor cells expressing the appropriate tumor-associated antigens can be effectively recognized and destroyed by these immune effector cells, which may result in dramatic clinical responses. Both the adoptive transfer of tumor-reactive CTL and active immunization designed to elicit CTL responses have been reported to lead to significant therapeutic anti-tumor responses in patients with cancer.

The T-cell induction portion of the invention may be performed using any of the approaches described in the invention, including cytokines and T-cell modulating agents used directly, or within adult stem cell delivery vehicles.

In some embodiments, induction of the T-cell response within a subject comprises injection of a stem cell in the subject. In some embodiments, the stem cell is an adult stem cell. In some embodiments, the stem cell is capable of excreting growth factors. In some embodiments, the stem cell produces antibodies, or growth factors capable of stimulating T-cell growth and expansion. In some embodiments, the stem cell is transformed with a lenti-virus or retrovirus. In some embodiments, the stem cell is transiently transfected with an artificial chromosome, virus or plasmid DNA. In some embodiments, the lenti-virus or retrovirus comprise a heterologous nucleic acid encoding a protein involved in T-cell activation. In some embodiments, the adult stem cells are permanently transformed (e.g. with lenti-virus or retrovirus), or transiently altered with artificial chromosomes, viruses or plasmid DNA, which results in the production of antibodies, growth factors, or other proteins as payloads that stimulate T-cell growth and expansion.

In some embodiments, the stem cell is injected into site of the tumor. In some embodiments, the stem cell is injected into the tumor.

Optimal T cell activation requires simultaneous signals through the T cell receptor and costimulatory molecules. The costimulatory molecule CD28, upon interaction with its ligands B7-1 and B7-2, plays a crucial role in initial T cell priming. However, the CD28-mediated T cell expansion is opposed by the B7-1/2 counter receptor, cytotoxic T lymphocyte associated antigen 4 (CTLA-4), which mitigates the proliferation of recently activated T cells. This sequential regulation of CD28 and CTLA-4 expression balances the activating and inhibitory signals and ensures the induction of an effective immune response, while protecting against the development of autoimmunity. Blocking of CTLA-4 with monoclonal antibodies has demonstrated some success in human clinical trials. Additional CD28 and B7 family members have been identified: PD-1 (programmed death-1), PD-L1 (programmed death ligand-1 or B7-H1), and PD-L2 (B7-DC). As in the CTLA-4/B7 system, the PD-1 interactions with PD-L1 and PD-L2 suppress both central and peripheral immune responses, and therefore, the PD-1 blockade is also being explored in clinical trials. In addition, numerous new agents targeting the inhibitory and activation pathways involved in T-cell modulation such as LAG-3, B7-H3, CD40, OX40, CD137 and others are in active development.

Accordingly, in some embodiments, T-cell induction comprises administration an agonist of an activating co-stimulatory molecule. In some embodiments, the method comprises administration of agonistic antibodies directed against activating co-stimulatory molecules. In some embodiments, T-cell induction comprises administration of agonistic antibodies against a co-stimulatory molecule selected from the group consisting of: CD28, OX40, GITR, CD137, CD27 and HVEM.

In some embodiments, T-cell induction comprises administration of a treatment that antagonizes negative co-stimulatory molecules. In some embodiments, the method comprises administration of blocking antibodies against negative co-stimulatory molecules. In some embodiments, T-cell induction comprises administration of blocking antibodies against a negative co-stimulatory molecule selected from the group consisting of: CTLA-1; PD-1, TIM-3, BTLA, VISTA and LAG-3. In some embodiments, T-cell induction comprises administration of CTLA-4 blocking antibodies. In some embodiments, T-cell induction comprises administration of PD-1 pathway inhibitors. In some embodiments, the inhibitor of the PD-1 pathway is selected from antibodies against PD-1 and soluble PD-1 ligand. In some embodiments, the inhibitors of the PD-1 pathway are selected from AMP-244, MEDI-4736, MPDL328 OA, and MIH1.

In some embodiments, T-cell induction comprises administration of a treatment that stimulates T-cell expansion. In some embodiments, a treatment that stimulates T-cell expansion comprises administration of cytokines. In some embodiments, a treatment that stimulates T-cell expansion comprises administration of cytokine-expressing stem cells.

Administration of Treatment Modalities

It is to be understood that the treatment modalities of the invention may be administered in any order. In some embodiments, step (a) is performed before step (b) and step (c). In some embodiments, step (b) is performed after step (c). In some embodiments, step (b) is performed before step (c). In some embodiments, any of the steps are performed concurrently.

The effective dosage of each of the treatment modalities employed in the combination therapy of the invention may vary depending on the particular treatment, compound or pharmaceutical composition employed, the mode of administration, the condition being treated, the severity of the condition being treated. Thus, the dosage regimen of the combination of the invention is selected in accordance with a variety of factors including the route of administration and the renal and hepatic function of the patient. A physician, clinician or veterinarian of ordinary skill can readily determine and prescribe the effective amount of the single active ingredients required to prevent, counter or arrest the progress of the condition. Optimal precision in achieving concentration of the active ingredients within the range that yields efficacy without toxicity requires a regimen based on the kinetics of the active ingredients' availability to target sites.

Methods of preparing pharmaceutical compositions comprising the relevant treatments disclosed herein are known in the art and will be apparent from the art, from known standard references, such as Remington's Pharmaceutical Sciences, Mack Publishing Company, Easton, Pa., 18th edition (1990).

It should be understood that the embodiments described herein are not limited to vaccinations or vaccinating per se, but also relate to generating an immune response or reaction to cancer cells. While the words "vaccine," "vaccination," or other like terms are used for convenience, it should be understood that such embodiments also relate to immune compositions, immunogenic compositions, immune response generation, immunization, etc., where absolute prophylactic immunity is not required or generated. For example, the embodiments referring to vaccination also can relate to generating or to assisting in creating an immunogenic or immune response against a tumor cell or tumor, regardless of whether that response results in absolute eradication or immunization against such tumor cell, tumor or the cancer.

The disclosures illustratively described herein may suitably be practiced in the absence of any element or elements, limitation or limitations, not specifically disclosed herein. Thus, for example, the terms "comprising," "including," containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

Other embodiments are set forth within the following claims.

What is claimed is:

1. A method for treating a solid tumor or hematologic malignancy in a subject, comprising:
   (a) injecting into the subject a composition comprising an adipose-derived stromal vascular fraction (SVF), which comprises stem cells, wherein:
      the stem cells comprise a lytic virus that kills tumor cells; and
      the lytic virus is a vaccinia virus; and
   (b) administering a treatment to the subject that activates a T-cell response within the subject, wherein:
      the treatment comprises administering a blocking antibody against a negative co-stimulatory molecule; and
      step (a) is performed before step (b).

2. The method of claim 1, further comprising treating the subject with radio-immunotherapy or chemotherapy.

3. The method of claim 1, wherein step (a) results in in situ vaccination of the subject against the tumor.

4. A method for treating a solid tumor or hematologic malignancy in a subject, comprising:
   (a) injecting into the subject a composition comprising adipose-derived stromal stem cells, wherein:

the adipose-derived stromal stem cells comprise a lytic virus that kills tumor cells; and the lytic virus is a vaccinia virus; and (b) administering a treatment to the subject that activates a T-cell response within the subject, wherein:

the treatment comprises administering a blocking antibody against a negative co-stimulatory molecule; and step (a) is performed before step (b).

5. The method of claim 4, wherein prior to step (a), the adipose-derived stromal stem cells are treated with a treatment selected from among:

a Toll-like receptor (TLR) agonist; intravenous immunoglobulin (IVIG); monocyte conditioned media; supernatant from neutrophil extracellular trap-exposed peripheral blood mononuclear cells; co-culture with monocytes; co-culture with monocytes that have been pretreated with IVIG; co-culture with T cells; co-culture with T cells that have been exposed to a T cell stimulus; co-culture with natural killer cells; peptidoglycan isolated from Gram-positive bacteria; lipoarabinomannan isolated from mycobacteria; zymosan isolated from a yeast cell wall; polyadenylic-polyuridylic acid; poly (IC); lipopolysaccharide; monophosphoryl lipid A; flagellin; Gardiquimod; Imiquimod; Resiquimod; oligonucleosides containing CpG motifs; and 23S ribosomal RNA.

6. The method of claim 4, wherein the adipose-derived stromal stem cells are autologous.

7. The method of claim 4, wherein the adipose-derived stromal stem cells are allogeneic.

8. The method of claim 1, wherein step (b) comprises administering blocking antibodies against negative co-stimulatory molecules selected from among PD-L1 and CTLA-4.

9. The method of claim 1, comprising administration of blocking antibodies against a negative co-stimulatory molecule selected from among CTLA-1, CTLA-4, PD-1, TIM-3, BTLA, VISTA, and LAG-3.

10. The method of claim 1, wherein the blocking antibody against a negative co-stimulatory molecule in step (b) comprises an inhibitor of the PD-1 pathway.

11. The method of claim 1, wherein the tumor is selected from among glioblastoma, breast carcinoma, lung carcinoma, prostate carcinoma, colon carcinoma, ovarian carcinoma, neuroblastoma, central nervous system tumor, and melanoma.

12. The method of claim 10, wherein the inhibitor of the PD-1 pathway is selected from antibodies against PD-1 or against soluble PD-1 ligand.

13. The method of claim 10, wherein the inhibitor of the PD-1 pathway is selected from AMP-244, MEDI-4736, MPDL3280A, or MIH1.

14. The method of claim 1, wherein step (b) comprises administering an anti-CTLA-4 antibody, or an anti-PD-L1 antibody, or an anti-PD-1 antibody.

15. The method of claim 1, wherein the subject had previously been treated with radiation therapy or chemotherapy or both.

16. The method of claim 1, further comprising treating the subject with radiation therapy or chemotherapy or both.

* * * * *